(12) United States Patent
Petersen

(10) Patent No.: US 8,708,900 B2
(45) Date of Patent: *Apr. 29, 2014

(54) LED DRIVE CIRCUIT AND METHOD FOR USING SAME

(71) Applicant: Covidien LP, Boulder, CO (US)

(72) Inventor: Ethan Petersen, Castro Valley, CA (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/750,805

(22) Filed: Jan. 25, 2013

(65) Prior Publication Data

US 2013/0137947 A1 May 30, 2013

Related U.S. Application Data

(63) Continuation of application No. 12/343,799, filed on Dec. 24, 2008, now Pat. No. 8,366,613.

(60) Provisional application No. 61/009,076, filed on Dec. 26, 2007.

(51) Int. Cl.
*A61B 1/06* (2006.01)

(52) U.S. Cl.
USPC .......................................... 600/249; 600/323

(58) Field of Classification Search
USPC ............... 600/249, 323, 309, 310, 322
See application file for complete search history.

(56) References Cited

U.S. PATENT DOCUMENTS

| | | | |
|---|---|---|---|
| 4,773,422 A * | 9/1988 | Isaacson et al. | 600/326 |
| 4,781,195 A | 11/1988 | Martin | |
| 5,575,284 A | 11/1996 | Athan et al. | |
| 5,645,059 A | 7/1997 | Fein et al. | |
| 5,861,013 A * | 1/1999 | Peck et al. | 607/28 |
| 5,873,898 A * | 2/1999 | Hemming et al. | 607/28 |
| 6,163,724 A * | 12/2000 | Hemming et al. | 607/28 |
| 6,360,113 B1 * | 3/2002 | Dettling | 600/322 |
| 6,381,479 B1 | 4/2002 | Norris | |
| 6,496,711 B1 | 12/2002 | Athan et al. | |
| 8,242,429 B2 * | 8/2012 | Sarpeshkar et al. | 250/214 A |
| 2005/0084202 A1 | 4/2005 | Smith et al. | |
| 2005/0234317 A1 | 10/2005 | Kiani | |
| 2007/0132692 A1 | 6/2007 | Yang | |
| 2007/0208240 A1 | 9/2007 | Nordstrom et al. | |
| 2009/0163784 A1 | 6/2009 | Sarpeshkar et al. | |

FOREIGN PATENT DOCUMENTS

| | | |
|---|---|---|
| EP | 0194105 A2 | 10/1986 |
| WO | 9403102 A1 | 2/1994 |

* cited by examiner

*Primary Examiner* — Thuy Vinh Tran
(74) *Attorney, Agent, or Firm* — Fletcher Yoder PC

(57) ABSTRACT

In various embodiments, there is provided an LED drive circuit and a method for using the same. Specifically, the present disclosure is directed to an LED drive circuit for pulse oximeters. In an embodiment, the LED drive circuit includes a current mirror configured to provide drive current to an LED of a sensor. Additionally, the method includes providing current to first and second current mirrors, wherein the first and second current mirrors are configured to control first and second light sources.

20 Claims, 4 Drawing Sheets

LED DRIVE CIRCUIT AND METHOD FOR USING SAME

CROSS-REFERENCE TO RELATED APPLICATIONS

This application is a continuation of U.S. patent application Ser. No. 12/343,799, filed Dec. 24, 2008, which claims the benefit of U.S. Provisional Application No. 61/009,076, filed Dec. 26, 2007, all of which are incorporated herein by reference in their entirety.

BACKGROUND

The present disclosure relates generally to LED drive circuits and, more particularly, to LED drive circuits used for pulse oximetry.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors may desire to monitor certain physiological characteristics of their patients. Accordingly, a wide variety of devices may have been developed for monitoring physiological characteristics of a patient. Such devices provide doctors and other healthcare personnel with the information they need to provide better healthcare for their patients.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically senses the absorption and/or scattering of the transmitted light in such tissue. One or more of the above physiological characteristics may then be calculated based upon the amount of light absorbed or scattered. More specifically, the light passed through the tissue is typically selected to be of one or more wavelengths that may be absorbed and/or scattered by the blood in an amount correlative to the amount of the blood constituent present in the blood. The amount of light absorbed and/or scattered may then be used to estimate the amount of blood constituent in the tissue using various algorithms. Changes in the amount of arterial blood in the tissue during a blood pressure pulse may change the amount and character of the light detected by the sensor's photodetector.

More specifically, within the field of pulse oximetry, the blood oxygen level of a patient may be determined by measuring the differential absorption of light produced by red and infrared emitters. Typically, the emitters are two types of LEDs that are turned on in sequence by an LED drive circuit which controls the activation of each LED at the proper time. However, LED drive circuits may use a large number of component parts. Each part may introduce a potential point of failure in manufacture and during the operation of the pulse oximeter. Furthermore, because of the large number of parts, LED drive circuits tend to be fairly large in size to accommodate the number of parts.

BRIEF DESCRIPTION OF THE DRAWINGS

Advantages of the disclosure may become apparent upon reading the following detailed description and upon reference to the drawings in which.

SUMMARY

Certain aspects commensurate in scope of embodiments are set forth below. It should be understood that these aspects are presented merely to provide the reader with a brief summary of certain forms the embodiments might take and that these aspects are not intended to limit the scope of the disclosure. Indeed, the disclosure may encompass a variety of aspects that may not be set forth below.

In accordance with one embodiment, there is provided an LED drive circuit for a pulse oximeter. The LED drive circuit may include a current mirror configured to supply a current to activate an LED of a pulse oximetry sensor.

In accordance with embodiment, there is provided a pulse oximetry monitor. The pulse oximetry monitor may include a light drive circuit comprising a first current mirror drive circuit with a first current input, and a second current mirror drive circuit with a second current input. The first and second current mirror drive circuits may be capable of alternately supplying current to at least two LEDs.

In accordance with an embodiment, there is provided a method of operating a pulse oximeter light drive circuit. The method includes providing a first current to a first current mirror, the first current mirror controlling a first light source and providing a second current to a second current mirror, the second current mirror controlling a second light source. The method further includes turning off current to both the first and second current mirrors for a period after each instance of either the first or second current mirrors being turned on.

DETAILED DESCRIPTION

One or more embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In an embodiment, the present disclosure describes techniques for providing drive current to emitters in a pulse oximetry system. Specifically, the techniques include using current mirrors in the drive circuit. The current mirrors may allow for a reduced number of component parts, thus reducing the size of the driving circuit as well as the cost of manufacturing the circuit and also facilitating the production of accurate current signals. Additionally, the component parts may be generic, low-cost resistors and transistors, as will be discussed in detail below.

Figure 1:
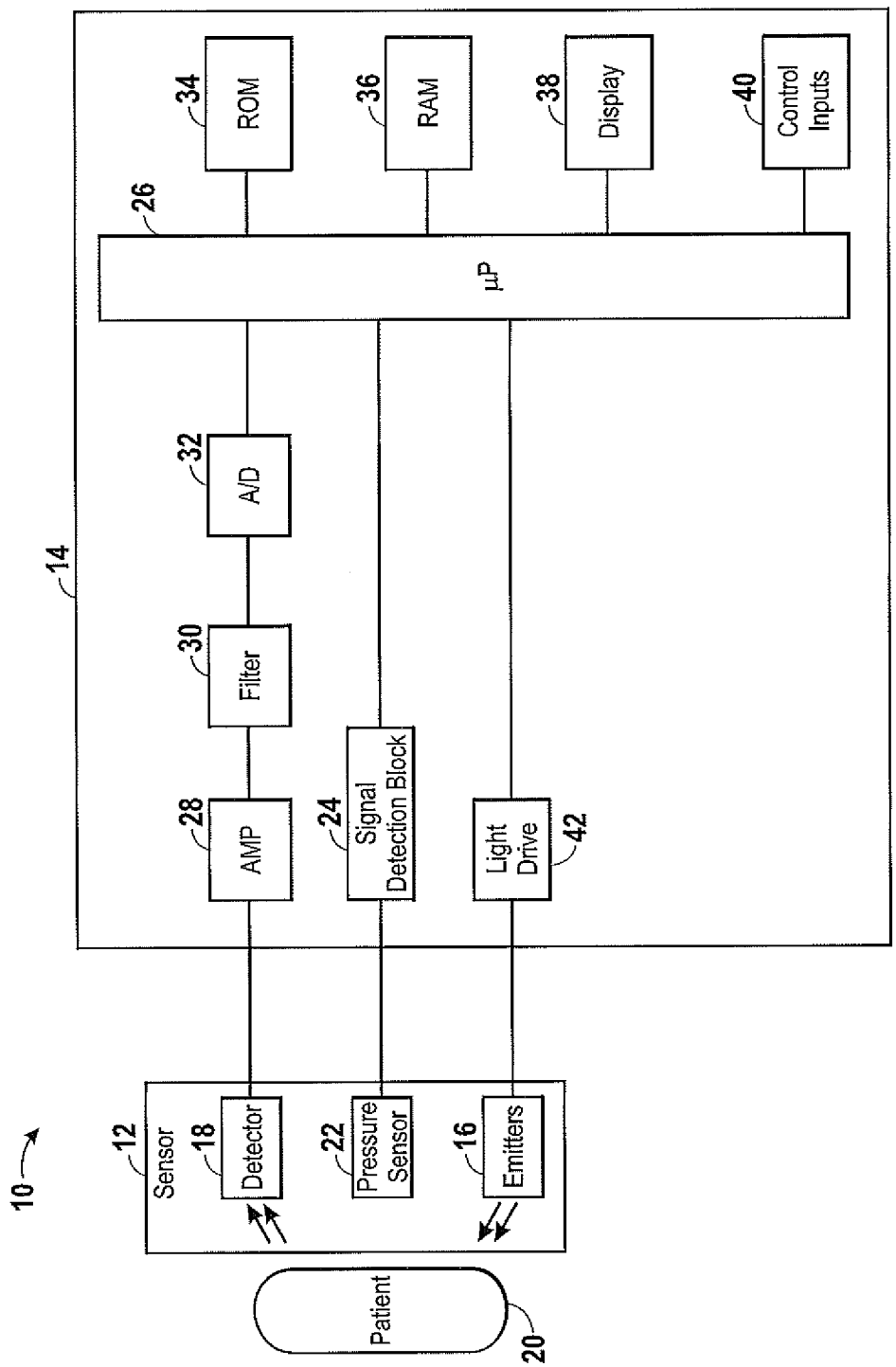
FIG. 1 illustrates a block diagram of a pulse oximetry system in accordance with an embodiment.

Turning to the figures and referring initially to FIG. 1, a block diagram of a pulse oximeter is illustrated in accordance with an embodiment, and is generally designated by the reference numeral 10. The block diagram 10 is an embodiment and an actual implementation may include more or fewer components as needed for a specific application.

In an embodiment, the pulse oximeter 10 includes a sensor 12 which is coupled to or integrated with a monitor 14. In an embodiment, the sensor includes emitters 16 which are configured to transmit electromagnetic radiation, such as light, for example. In accordance with an embodiment, the emitters 16 may include an LED that emits electromagnetic radiation in the red region of the electromagnetic spectrum and an LED that emits electromagnetic radiation in the infrared region of the electromagnetic spectrum. The emitted radiation transmitted from the emitters 16 into a patient's tissue is detected by a detector 18 after the radiation has passed through blood perfused tissue of a patient 20. The detector 18 generates a photoelectrical signal correlative to the amount of radiation detected.

In accordance with an embodiment, the sensor 12 may include a pressure sensor 22 which provides feedback regarding to the monitor 14 via a signal detection block 24 to a microprocessor 26 in the monitor 14 to indicate whether an appropriate pressure is being applied to the sensor 12 by the patient 20. Exemplary pressure sensors are discussed in detail in U.S. Provisional Application Nos. 61/009,095 and 61/009,075, entitled "Pulse Oximetry Sensor with a Pressure Sensor," which are incorporated herein by reference in its entirety for all purposes.

The signal generated by the detector 18 is provided to the monitor 14 where it may be amplified (by amplifier 28), filtered (by filter 30), and digitized (by A/D converter 32), in an embodiment. In an embodiment, the digitized signal may be provided to a microprocessor 26 for further processing and for the computing of physiological parameters related to the patient 20. For example, the microprocessor 26 may compute a percent oxygen saturation of hemoglobin and/or a pulse rate, among many other physiological parameters.

In an embodiment, the monitor may include other component parts such as a read-only memory (ROM) 34, which may store operating software for the monitor and algorithms for computing physiological parameters. The ROM 34 may include many types of non-volatile memory. Additionally, a random access memory (RAM) 36 may be provided to allow for the storage of digitized data including the computed physiological parameters, for example.

In an embodiment, a display 38 may be integrated into the monitor 14 to allow for display of the computed physiological parameters. In another embodiment, the monitor 14 may include a port (not shown) or connector to allow a separate display device to connect into the monitor 14. Control inputs 40 may also be provided to allow a user to interface with the monitor 14.

In addition to computing physiological parameters, the microprocessor 26 may control the timing and intensity of the emitted electromagnetic radiation of the emitters 16 via a light drive circuit 42. In accordance with embodiments, the light drive circuit 42 may have a lower part count when compared with light drives of the prior art. The reduced part count may reduce the size and complexity of the light drive circuit 42 and, thus, the size of the monitor 14. Indeed, in accordance with an embodiment, the monitor 14 and the sensor may be integrated into a single unit that may be handheld, as discussed in detail in the patent application mentioned above.

Figure 2:
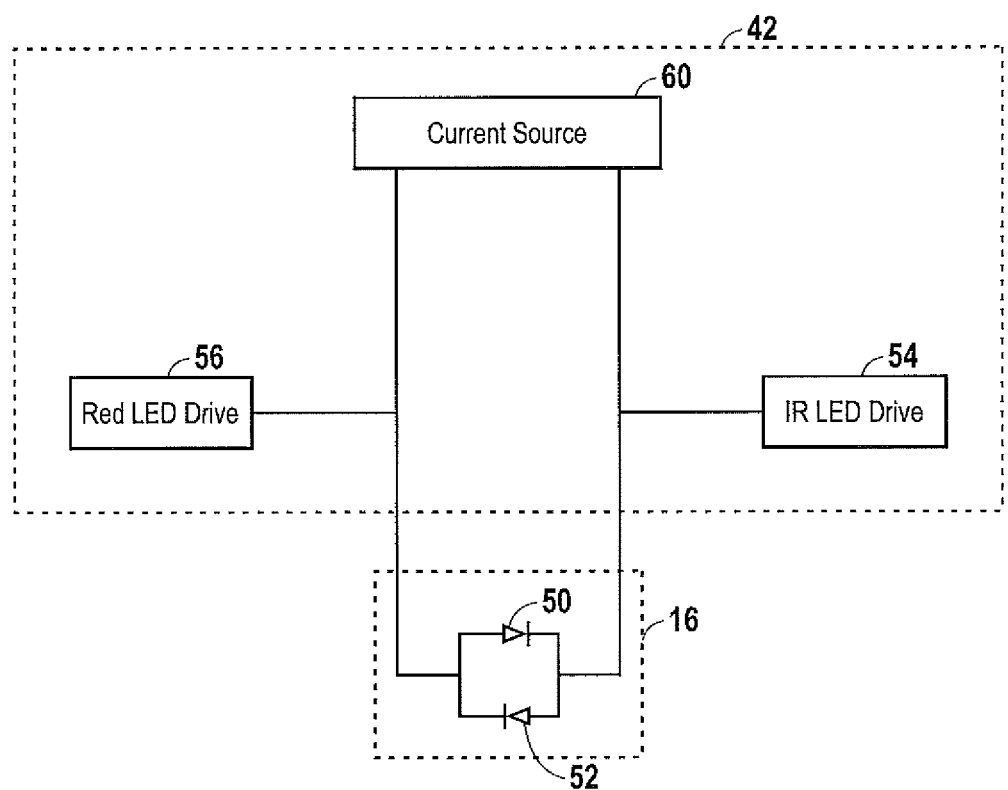
FIG. 2 illustrates a block diagram of a light drive circuit for the pulse oximetry system of FIG. 1 in accordance with an embodiment.

Referring to FIG. 2, a block diagram of the light drive circuit 42 is illustrated with the emitters 16 of the sensor 12 in accordance with an embodiment. As shown, the emitters 16 include two LEDs (a red LED 50 and an IR LED 52) coupled in a back-to-back configuration. In an embodiment, the IR LED drive 54 and the Red LED drive 56 are current mirror circuits which amplify the output current of a digital-to-analog converter (DAC) to achieve the 0-50 mA, which may be needed for a pulse oximetry LED drive. This may allow the circuit to be driven by any microcontroller providing a current output DAC, such as a C8051F353 microcontroller which has a DAC built-in. As such, in one embodiment, the microprocessor 26 may include a C8051F353 microcontroller. The IR LED Drive 54 and the Red LED drive 56 may be alternatively activated by the microcontroller's output current. The current source 60 may be configured to steer current through the LEDs 50 and 52 without the use of additional timing circuitry, as illustrated in FIG. 3 and as discussed in detail below.

Figure 3:
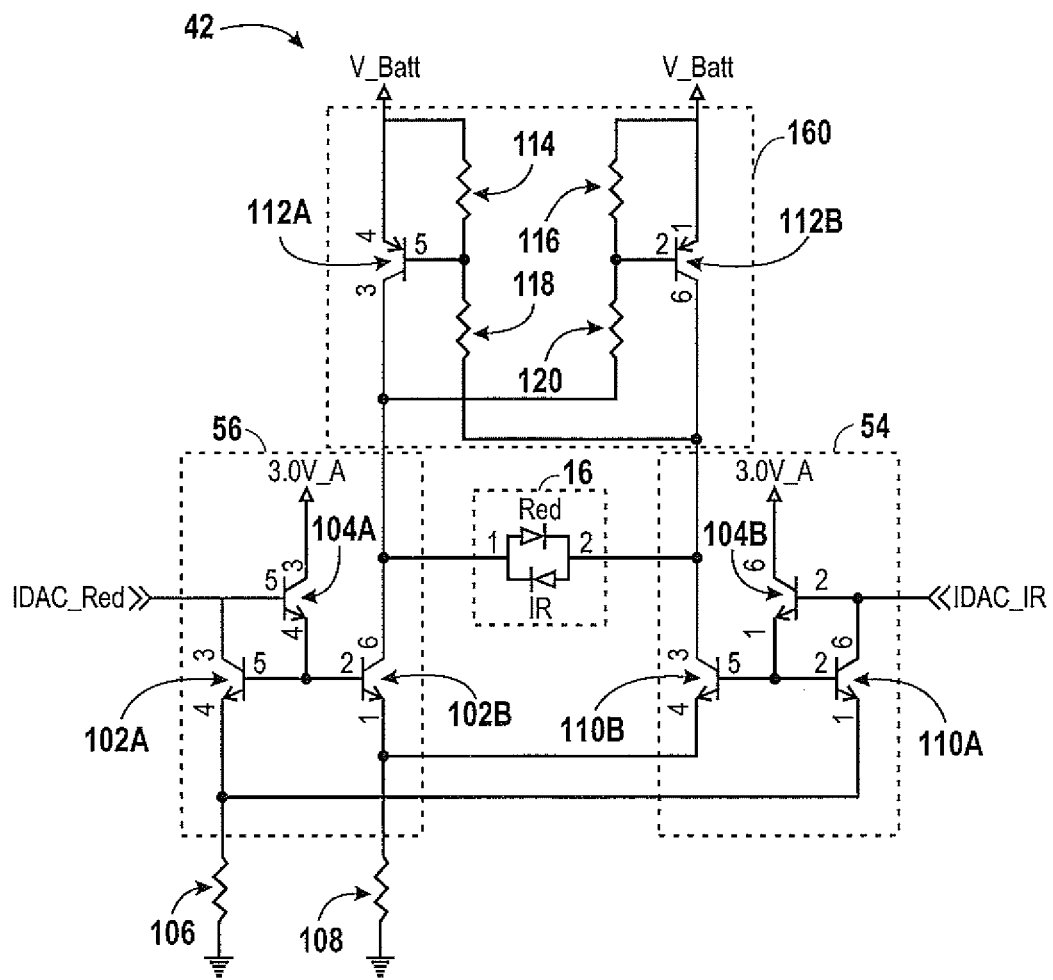
FIG. 3 is a schematic diagram of the light drive circuit of FIG. 2 in accordance with an embodiment.

Referring to FIG. 3, a detailed schematic diagram of the light drive circuit 42 is illustrated in accordance with an embodiment. The diagram illustrates each of the IR LED Drive 54 and the Red LED Drive 56 as being current mirrors. Specifically, as illustrated the IR LED Drive 54 and the Red LED Drive 56 are illustrated as bi-polar junction transistor (BJT) mirrors with base current compensation. Those of ordinary skill in the art will recognize that there are several alternative current mirror configurations that may be implemented. Additionally, a current mirror may be implemented using metallic-oxide semiconductor field effect transistors (MOSFETs) instead of BJTs.

In an embodiment, each of the IR LED Drive 54 and the Red LED Drive 56 includes three NPN BJT transistors. Specifically, the Red LED Drive 56 includes a pair of transistors 102A-B coupled in a parallel configuration and a transistor 104A. In an embodiment, the pair of transistors 102A-B share a common node for their respective base leads. To facilitate operation of the current mirror circuit, the temperature of the paired transistors 102A-B may be approximately equal. To accomplish this, the transistors 102A-B may be coupled together, located in close proximity to each other within the circuit, or they may be included in a common transistor package that provides two transistors, such as a MBT3904DW1T1 dual transistor, for example. The use of the dual transistor packaging provides an advantage of not only maintaining approximately consistent temperatures, but also further reduces the number of components.

In an embodiment, the emitter lead of the transistor 104A is coupled to the base leads of both transistors 102A-B. Additionally, the collector lead of the transistor 104A is coupled to a voltage source which may provide a designated voltage level, such as 3 volts, for example, to the Red LED Drive 56. In an embodiment, the base lead of the transistor 104A is coupled to the collector lead of the transistor 102A and also to a current output of the microprocessor 26. As discussed above, the microprocessor 26 may provide multiple DAC current outputs that can serve as the drive signals for the light drive circuit 42 of FIG. 1. Specifically, the microprocessor may provide an IDAC_Red current to the Red LED Drive 56 and an IDAC_IR current to the IR LED Drive 54.

In an embodiment, the collector lead of transistor 102B may be coupled to both the emitters 16 and the current source 60. The emitter leads of the transistors 102A-B are each coupled to ground via resistors 106 and 108, respectively. The resistors may have any appropriate value to achieve a desired current. For example, in accordance with an embodiment, resistor 106 may be a 280 ohm resistor and resistor 108 may be a 10 ohm resistor. When a IDAC_Red current is received by the Red LED Drive 56, an amplified current is induced in the transistor 102B which causes the Red LED 50 to emit electromagnetic radiation.

In an embodiment, the IR LED Drive 54 is similar in structural aspects to the Red LED Drive 56. In particular, the IR LED Drive 54 and the Red LED Drive 56 share resistors 106 and 108. Additionally, in accordance with an embodiment, a transistor 104B is a second transistor of a dual transistor package shared with transistor 104A. The IR LED Drive 54 also includes NPN BJT transistors 110A-B which are coupled together in a parallel configuration, similar to the transistors 102A-B, with their base leads coupled together as shown. The transistor 110B is coupled to the current source 60 and the emitter 16. The IDAC_IR current activates the IR LED Drive 54 and induces an amplified current in the transistor 110B to cause the IR LED 52 to emit electromagnetic radiation.

In an embodiment, the current source 60 includes a pair of PNP BJT transistors 112A-B coupled in parallel. As with the other transistor pairs in the diagram 100, the transistor 112A-B may be included in a dual transistor package, such as the MBT3906DW1T1 package, for example, to reduce the number of component parts in the circuit. The collector leads of each of the transistors 112A-B are coupled to a voltage source such a battery, in an embodiment.

In an embodiment, the emitter leads of each of the transistors 112A-B are also coupled to resistors 114 and 116, respectively, which are coupled between the emitter and base leads of the respective transistors 112A-B. For example, resistor 114 is coupled between the emitter and base leads of the transistor 112A, while the resistor 116 is coupled to the emitter and base leads of transistor 112B. The resistors 114 and 116 may have the same resistance value, such as 15 kilo ohms, for example.

In an embodiment, the base leads of the transistors 112A-B are also coupled resistors 118 and 120, respectively. The resistors 118 and 120 are coupled between the base lead of a first transistor and a collector lead of a second transistor. Specifically, the resistor 118 is coupled between the base lead of transistor 112A and the collector lead of the transistor 112B. Similarly, the resistor 120 is coupled between the base lead of the transistor 112B and the collector lead of transistor 112A. The resistors 118 and 120 may have approximately the same resistive value, such as 604 Ohms for example. In alternative embodiments, the resistive values for the resistors 114, 116, 118 and 120 may vary.

In an embodiment, the collector leads of the current source 60 are coupled to the emitters 16 and the Red LED Drive 56 and IR LED Drive 54. Specifically, as shown, the collector of transistor 112A is coupled to the collector of transistor 102B, while the collector lead of transistor 112B is coupled to the collector lead of transistor 110B. Current flow, for causing the emitters 16 to emit radiation, however follows either a path from transistor 112A through the IR emitter 52 and the transistor 110B or a path from transistor 112B through the red emitter 50 and the transistor 102B. As discussed above, the IDAC_Red or IDAC_IR currents determine the timing. In an embodiment, there is no additional timing signals necessary for the current source 60.

In an embodiment, the microcontroller 26 may provide a current output to activate the IR LED Drive 54 and the Red LED Drive 56. Thus, the microcontroller 26 may control the timing of the red and IR LEDs 50 and 52, respectively. In an embodiment, the red LED 50 and the IR LED 52 may alternatively emit radiation, with dark periods (where neither LED is emitting) in between turns.

Figure 4:
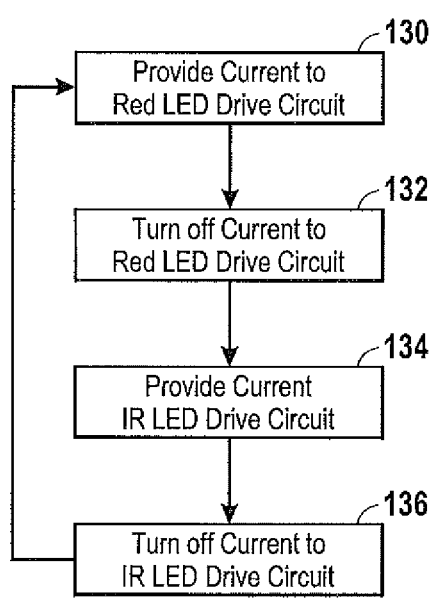
FIG. 4 illustrates a flow chart for operation of the light drive circuit in accordance with an embodiment.

FIG. 4 illustrates a flow chart for operation of the light drive circuit 42 in accordance with embodiments. Specifically, current may initially be provided from the microcontroller 26 to the Red LED Drive circuit 56, as indicated at block 130. Concurrently, the detector 18 of FIG. 1 takes measurements of detected light and provides the measurements to the monitor 14 for processing. In an embodiment, the microcontroller 26 then turns off the current to the Red LED Drive circuit 56 to allow for a dark period, as indicated at block 132. No measurements are taken during this period. Current is then provided to the IR LED Drive circuit 54, as indicated at block 134. The detector 18 again takes measurements of detected light and passes the measurements to the monitor 14 for processing. The current to the IR LED Drive circuit 54 is then turned off to allow for a dark state.

In an embodiment, once the monitor 14 has received the measurements that were taken when current was provided to both drive circuits 54 and 56, the monitor 14 may compute physiological parameters. Meanwhile, the microcontroller 26 will repeat the sequence shown in FIG. 4 to allow for additional measurements to be made. As such, the microcontroller 26 may control the timing of the light drive circuit 42 via the IDAC_Red and IDAC_IR current signals.

As mentioned earlier, the present disclosure provide for a dramatic reduction in component parts for the light drive circuit 42 over previous light drives for pulse oximeters. As FIG. 3 illustrates, the light drive circuit 42 may require merely 10 component parts when dual transistor packages are used, which may significantly reduce the amount of time required to manufacture the light drive circuit 42. Additionally, the parts implemented may be low cost, generic parts that significant reduce the cost of the light drive circuit 42 and, consequently, the monitor 14 and the pulse oximeter system 10. As such, the techniques described herein provide minimize material costs as well as assembly costs.

While the disclosure may be conducive to various modifications and alternative forms, embodiments have been shown by way of example in the drawings and have been described in detail herein. However, it should be understood that the disclosure is not intended to be limited to the particular embodiments disclosed. Indeed, the present disclosure may not only be applied to measurements of blood oxygen saturation, but also for the measurement and/or analysis of other blood constituents using principles of pulse oximetry. For example, using the same, different, or additional wavelengths, the present disclosure may be utilized for the measurement and/or analysis of carboxyhemoglobin, met-hemoglobin, total hemoglobin, intravascular dyes, and/or water content, among many different physiological parameters. As such, the disclosure is to cover all modifications, equivalents, and alternatives falling within the spirit and scope of the invention as defined by the following appended claims.

What is claimed is:

1. An LED drive circuit for a medical device comprising:
  a first current mirror configured to supply a first current to activate a first LED of a sensor, wherein the first current mirror comprises a plurality of transistors, wherein one of the transistors of the first current mirror is coupled to a DAC output of a microcontroller.

2. The LED drive circuit of claim 1, further comprising a current source coupled to the first current mirror to supply the first current to the first LED of the sensor.

3. The LED drive circuit of claim 2, wherein the current source comprises two PNP BJTs.

4. The LED drive circuit of claim 1, wherein the first current mirror comprises metallic-oxide semiconductor field effect transistors (MOSFETs).

5. The LED drive circuit of claim 1, wherein the DAC output of the microcontroller controls timing of the LED circuit.

6. The LED drive circuit of claim 1, wherein the plurality of transistors comprises three NPN bipolar junction transistors (BJTs).

7. The LED drive circuit of claim 6, wherein a first and second NPN BJT of the first current mirror have their respective base leads electrically coupled together.

8. The LED drive circuit of claim 7, wherein the first NPN BJT of the first current mirror is coupled to the DAC output of the microcontroller.

9. The LED drive circuit of claim 7, wherein the second NPN BJT of the first current mirror is coupled to a current source and the first LED of the sensor.

10. The LED drive current of claim 7, wherein the first and second NPN BJTs are paired in a dual transistor package.

11. The LED drive circuit of claim 1, comprising a second current mirror, wherein the first current mirror supplies the first current to the first LED of the sensor and the second current mirror supplies a second current to a second LED of the sensor.

12. The LED drive circuit of claim 1, wherein the first current mirror is configured with base current compensation.

13. A monitor for measuring a physiological parameter comprising:
    a light drive circuit comprising:
    a first current mirror drive circuit with a first current input;
    a second current mirror drive circuit with a second current input, wherein the first and second current mirror drive circuits are configured to alternately supply current to at least two light sources; and
    wherein the first current mirror drive circuit or the second current mirror drive circuit, or both, are configured to amplify an output current provided by a microcontroller.

14. The monitor of claim 13, wherein the at least two light sources comprise a first LED and a second LED, and wherein the first current mirror drive circuit is configured to provide current to the first LED and the second current mirror drive circuit is configured to provide current to the second LED.

15. The monitor of claim 14, further comprising a current source coupled to both the first and second current mirror drive circuits, and configured to provide current to the first and second LEDs.

16. The monitor of claim 13, further comprising a microprocessor configured to provide first and second current outputs to the first and second current mirror drive circuits, respectively.

17. The monitor of claim 13, wherein the first and second current mirror drive circuits are configured with base current compensation.

18. A method of operating a light drive circuit for a device for measuring a physiological parameter comprising:
    providing a first current to a first constant current source, the first constant current source configured to control a first light source;
    providing a second current to a second constant current source, the second constant current source configured to control a second light source; and
    turning off current to both the first and second constant current sources for a period after each instance of either the first or second constant current sources being turned on;
    wherein providing first and second currents comprises providing first and second output currents.

19. The method of claim 18, further comprising providing a third current from a current source coupled to both the first and second constant current sources.

20. The method of claim 18, wherein providing the first current source to the first constant current source comprises providing the first current source to a first current mirror, providing the second current source to the second constant current source comprises providing the second current source to a second current mirror, and turning off current to both the first and second constant current sources for the period after each instance of either the first and second current constant current sources being turned on comprises turning off current to both the first and second current mirrors for the period after each instance of either the first or second current mirrors being turned on.

* * * * *